(12) United States Patent
Presta et al.

(10) Patent No.: US 11,230,608 B2
(45) Date of Patent: Jan. 25, 2022

(54) ANTI-GLYCAN ANTIBODIES AND USES THEREOF

(71) Applicant: PTM Therapeutics, Inc., San Mateo, CA (US)

(72) Inventors: Leonard Presta, San Francisco, CA (US); Tony Liang, San Mateo, CA (US); Jennifer Cheng, San Mateo, CA (US)

(73) Assignee: PTM Therapeutics, Inc., San Mateo, CA (US)

( * ) Notice: Subject to any disclaimer, the term of this patent is extended or adjusted under 35 U.S.C. 154(b) by 0 days.

(21) Appl. No.: 17/203,650

(22) Filed: Mar. 16, 2021

(65) Prior Publication Data

US 2021/0292432 A1 Sep. 23, 2021

Related U.S. Application Data

(60) Provisional application No. 62/990,927, filed on Mar. 17, 2020, provisional application No. 63/037,374, filed on Jun. 10, 2020, provisional application No. 63/074,956, filed on Sep. 4, 2020.

(51) Int. Cl.

| C07K 16/00 | (2006.01) |
|---|---|
| C07K 16/30 | (2006.01) |
| A61P 1/00 | (2006.01) |
| A61K 39/00 | (2006.01) |

(52) U.S. Cl.
CPC ............ *C07K 16/3076* (2013.01); *A61P 1/00* (2018.01); *A61K 2039/505* (2013.01); *C07K 2317/24* (2013.01); *C07K 2317/92* (2013.01)

(58) Field of Classification Search
None
See application file for complete search history.

(56) References Cited

U.S. PATENT DOCUMENTS

2014/0322825 A1 10/2014 Pancer et al.

OTHER PUBLICATIONS

Almagro & Fransson, Frontiers in Bioscience 2008; 13:1619-33 (Year: 2008).*
Padlan (Advances in Protein Chemistry, 1996, 49:57-133) (Year: 1996).*
Berglund et al, Protein Science, 2008, 17:606-613 (Year: 2008).*
Corada (Blood, 2001; 97:1679-84) (Year: 2001).*
Kulkarni-Kale et al. Nucleic Acid Research, 2005, 33:W168-W171 (Year: 2005).*
Arends et al., (1983). "Monoclonal Antibody (1116 NS 19-9) Defined Monosialoganglioside (Gica) in Colorectal Carcinoma in Relation to Stage, Histopathology and DNA Flow Cytometry," Int. J. Cancer, 32:289-293.
Brazil et al., (2010). "Neutrophil Migration across Intestinal Epithelium: Evidence for a Role of CD44 in Regulating Detachment of Migrating Cells from the Luminal Surface," J Immunol, 185:7026-2036.
Brazil et al., (2013). "alpha3/4 Fucosyltransferase 3-Dependent Synthesis of Sialyl Lewis A on CD44 Variant Containing Exon 6 Mediates Polymorphonuclear Leukocyte Detachment from Intestinal Epithelium during Transepithelial Migration," J Immunol, 191:4804-4817.
Dube et al., (2005). "Glycans in cancer and inflammation—potential for therapeutics and diagnostics," Nat Rev Drug Discovery, 4:477-88.
Fuster et al., (2005). "The sweet and sour of cancer: glycans as novel therapeutic targets," Nat Rev Cancer, 5:526-42.
Graham et al., (1977). "Characteristics of a Human Cell Line Transformed by DNA from Human Adenovirus Type 5," J. Gen Virol., 36:59-72.
Haji-Ghassemi et al., (2015). "Antibody recognition of carbohydrate epitopes," Glycobiology, 25(9):920-952.
Jefferies et al., (2009). "Human immunoglobulin allotypes: Possible implications for immunogenicity," MAbs, 1(4):332-338.
Kelm et al., (Apr. 2019). "Targeting Epithelial Expressed Sialyl Lewis A Improves Intestinal Mucosal Wound Healing and Protects Against Colitis," presented during Experimental Biology Meeting 2019, Orlando, FL, USA, 1 page.
Kelm et al., (2020). "Targeting epithelium-expressed sialyl Lewis glycans improves colonic mucosal wound healing and protects against colitiss," JCI Insight, 5(12):e135843, 14 pages.
Koprowski et al., (1979). "Colorectal Carcinoma Antigens Detected by Hybridoma Antibodies," Somatic Cell Genetics, 5:957-972.
Magnani et al., (1981). "A Monosialoganglioside Is a Monoclonal Antibody-Defined Antigen of Colon Carcinoma," Science, 212(3):55-56.
Mather et al., (1982). "Culture of Testicular Cells in Hormone-Supplemented Serum-Free Medium," Annals N.Y. Acad. Sci., 383:44-68.
Mather, (1980). "Establishment and characterization of two distinct mouse testicular epithelial cell lines," Biol. Reprod., 23:243-251.
Urlaub et al., (1980). "Isolation of Chinese hamster cell mutants deficient in dihydrofolate reductase activity," Proc. Natl. Acad. Sci. USA, 77:4216-20.

(Continued)

*Primary Examiner* — Meera Natarajan
(74) *Attorney, Agent, or Firm* — Morrison & Foerster LLP (57) ABSTRACT

The present disclosure provides antibodies, or an antigen binding portion thereof, that bind to sLeA and sLeC, as well as polynucleotides, vectors, host cells, pharmaceutical compositions, and methods related thereto.

27 Claims, 3 Drawing Sheets

Specification includes a Sequence Listing.

(56) References Cited

OTHER PUBLICATIONS

International Search Report and Written Opinion for International Application No. PCT/US2021/022627, dated Jul. 12, 2021, 17 pages.
Liang et al., (2021). "Validation of Hptm-001, a Humanized Candidate Therapeutic Antibody for Promoting Mucosal Wound Healing in Ibd," Gastroenterology, 160(3):S50.
Liang et al., (2021). "Validation of Hptm-001, a Humanized Candidate Therapeutic Antibody for Promoting Mucosal Wound Healing in Ibd," HHS Public Access Author Manuscript, 27(1):S37, 2 pages.

* cited by examiner

SEQUENCE LISTING

<160> NUMBER OF SEQ ID NOS: 19

<210> SEQ ID NO 1
<211> LENGTH: 115
<212> TYPE: PRT
<213> ORGANISM: Artificial Sequence
<220> FEATURE:
<223> OTHER INFORMATION: Synthetic Construct

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Asn
            20                  25                  30

Ala Met Ser Trp Val Arg Gln Ala Pro Gly Lys Gly Leu Glu Trp Val
        35                  40                  45

Ser Arg Leu Arg Pro Lys Ser Asp Asn Tyr Ala Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Gly Thr Gly Phe Trp Gly Gln Gly Thr Val Thr
            100                 105                 110

Val Ser Ser
        115

<210> SEQ ID NO 2
<211> LENGTH: 115
<212> TYPE: PRT
<213> ORGANISM: Artificial Sequence
<220> FEATURE:
<223> OTHER INFORMATION: Synthetic Construct

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Asn
            20                  25                  30

Ala Met Ser Trp Val Arg Gln Ala Pro Gly Lys Gly Leu Glu Trp Val
        35                  40                  45

Ala Arg Leu Arg Pro Lys Ser Asp Asn Tyr Ala Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Thr Gly Thr Gly Phe Trp Gly Gln Gly Thr Thr Leu Thr
            100                 105                 110

Val Ser Ser
        115

<210> SEQ ID NO 3
<211> LENGTH: 115
<212> TYPE: PRT
<213> ORGANISM: Artificial Sequence
<220> FEATURE:
<223> OTHER INFORMATION: Synthetic Construct

<400> SEQUENCE: 3

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Asn
            20                  25                  30

Ala Met Ser Trp Val Arg Gln Ala Pro Gly Lys Gly Leu Glu Trp Val
        35                  40                  45

Ala Arg Leu Arg Pro Lys Ser Asp Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Thr Gly Thr Gly Phe Trp Gly Gln Gly Thr Leu Thr
            100                 105                 110

Val Ser Ser
        115

<210> SEQ ID NO 4
<211> LENGTH: 115
<212> TYPE: PRT
<213> ORGANISM: Artificial Sequence
<220> FEATURE:
<223> OTHER INFORMATION: Synthetic Construct

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Asn
            20                  25                  30

Ala Met Ser Trp Val Arg Gln Ala Pro Gly Lys Gly Leu Glu Trp Val
        35                  40                  45

Ala Arg Leu Arg Pro Lys Ser Asp Asn Tyr Ala Thr Tyr Tyr Ala Asp
    50                  55                  60

Ser Val Lys Gly Arg Phe Thr Ile Ser Arg Asp Asp Ser Thr Ser Thr
65                  70                  75                  80

Leu Tyr Leu Gln Met Asn Ser Leu Arg Ala Glu Asp Thr Ala Val Tyr
                85                  90                  95

Tyr Cys Val Thr Gly Thr Gly Phe Trp Gly Gln Gly Thr Leu Thr
            100                 105                 110

Val Ser Ser
        115

<210> SEQ ID NO 5
<211> LENGTH: 113
<212> TYPE: PRT
<213> ORGANISM: Artificial Sequence
<220> FEATURE:
<223> OTHER INFORMATION: Synthetic Construct

<400> SEQUENCE: 5

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Thr Ser Thr Arg Glu Ser Gly Val
```

```
                    50                  55                  60
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                 85                  90                  95

Asp Tyr Thr Ser Pro Tyr Thr Phe Gly Gln Gly Thr Lys Leu Glu Ile
            100                 105                 110

Lys

<210> SEQ ID NO 6
<211> LENGTH: 113
<212> TYPE: PRT
<213> ORGANISM: Artificial Sequence
<220> FEATURE:
<223> OTHER INFORMATION: Synthetic Construct

<400> SEQUENCE: 6

Asp Ile Val Met Thr Gln Ser Pro Asp Ser Leu Ala Val Ser Leu Gly
  1               5                  10                  15

Glu Arg Val Thr Met Asn Cys Lys Ser Ser Gln Ser Leu Leu Asn Ser
                 20                  25                  30

Gly Asn Gln Lys Asn Tyr Leu Thr Trp Tyr Gln Gln Lys Pro Gly Gln
             35                  40                  45

Pro Pro Lys Leu Leu Ile Tyr Trp Thr Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Val Gln Ala Glu Asp Val Ala Val Tyr Tyr Cys Gln Asn
                 85                  90                  95

Asp Tyr Thr Ser Pro Tyr Thr Phe Gly Gln Gly Thr Lys Leu Glu Ile
            100                 105                 110

Lys

<210> SEQ ID NO 7
<211> LENGTH: 113
<212> TYPE: PRT
<213> ORGANISM: Artificial Sequence
<220> FEATURE:
<223> OTHER INFORMATION: Synthetic Construct

<400> SEQUENCE: 7

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Leu Leu Asn Ser
                 20                  25                  30

Gly Asn Gln Lys Asn Tyr Leu Thr Trp Tyr Gln Gln Lys Pro Gly Gln
             35                  40                  45

Pro Pro Lys Leu Leu Phe Tyr Trp Thr Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                 85                  90                  95

Asp Tyr Thr Ser Pro Tyr Thr Phe Gly Gln Gly Thr Lys Leu Glu Ile
            100                 105                 110

Lys
```

<210> SEQ ID NO 8
<211> LENGTH: 113
<212> TYPE: PRT
<213> ORGANISM: Artificial Sequence
<220> FEATURE:
<223> OTHER INFORMATION: Synthetic Construct

<400> SEQUENCE: 8

```
Asp Ile Val Met Thr Gln Ser Pro Asp Ser Leu Ala Val Ser Leu Gly
1               5                   10                  15

Glu Arg Val Thr Met Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Phe Tyr Trp Thr Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Asn
                85                  90                  95

Asp Tyr Thr Ser Pro Tyr Thr Phe Gly Gln Gly Thr Lys Leu Glu Ile
            100                 105                 110

Lys
```

<210> SEQ ID NO 9
<211> LENGTH: 113
<212> TYPE: PRT
<213> ORGANISM: Artificial Sequence
<220> FEATURE:
<223> OTHER INFORMATION: Synthetic Construct

<400> SEQUENCE: 9

```
Asp Ile Val Met Thr Gln Ser Pro Asp Ser Leu Ala Val Ser Leu Gly
1               5                   10                  15

Glu Arg Val Thr Met Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Phe Tyr Trp Thr Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Thr Ser Pro Tyr Thr Phe Gly Gln Gly Thr Lys Leu Glu Ile
            100                 105                 110

Lys
```

<210> SEQ ID NO 10
<211> LENGTH: 113
<212> TYPE: PRT
<213> ORGANISM: Artificial Sequence
<220> FEATURE:
<223> OTHER INFORMATION: Synthetic Construct

<400> SEQUENCE: 10

```
Asp Ile Val Met Thr Gln Ser Pro Asp Ser Leu Ala Val Ser Leu Gly
1               5                   10                  15
```

```
Glu Arg Val Thr Met Asn Cys Lys Ser Ser Gln Ser Leu Leu Gln Ser
                20                  25                  30

Gly Asn Gln Lys Asn Tyr Leu Thr Trp Tyr Gln Lys Pro Gly Gln
         35                  40                  45

Pro Pro Lys Leu Leu Phe Tyr Trp Thr Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Thr Ser Pro Tyr Thr Phe Gly Gln Gly Thr Lys Leu Glu Ile
            100                 105                 110

Lys
```

```
<210> SEQ ID NO 11
<211> LENGTH: 113
<212> TYPE: PRT
<213> ORGANISM: Artificial Sequence
<220> FEATURE:
<223> OTHER INFORMATION: Synthetic Construct

<400> SEQUENCE: 11

Asp Ile Val Met Thr Gln Ser Pro Asp Ser Leu Ala Val Ser Leu Gly
 1               5                  10                  15

Glu Arg Val Thr Met Asn Cys Lys Ser Ser Gln Ser Leu Leu Ser Ser
                20                  25                  30

Gly Asn Gln Lys Asn Tyr Leu Thr Trp Tyr Gln Lys Pro Gly Gln
         35                  40                  45

Pro Pro Lys Leu Leu Phe Tyr Trp Thr Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Thr Ser Pro Tyr Thr Phe Gly Gln Gly Thr Lys Leu Glu Ile
            100                 105                 110

Lys
```

```
<210> SEQ ID NO 12
<211> LENGTH: 10
<212> TYPE: PRT
<213> ORGANISM: Artificial Sequence
<220> FEATURE:
<223> OTHER INFORMATION: Synthetic Construct

<400> SEQUENCE: 12

Gly Phe Thr Phe Ser Thr Asn Ala Met Ser
 1               5                  10
```

```
<210> SEQ ID NO 13
<211> LENGTH: 12
<212> TYPE: PRT
<213> ORGANISM: Artificial Sequence
<220> FEATURE:
<223> OTHER INFORMATION: Synthetic Construct

<400> SEQUENCE: 13

Arg Leu Arg Pro Lys Ser Asp Asn Tyr Ala Thr Tyr
 1               5                  10
```

<210> SEQ ID NO 14
<211> LENGTH: 6
<212> TYPE: PRT
<213> ORGANISM: Artificial Sequence
<220> FEATURE:
<223> OTHER INFORMATION: Synthetic Construct

<400> SEQUENCE: 14

Val Thr Gly Thr Gly Phe
1               5

<210> SEQ ID NO 15
<211> LENGTH: 17
<212> TYPE: PRT
<213> ORGANISM: Artificial Sequence
<220> FEATURE:
<223> OTHER INFORMATION: Synthetic Construct

<400> SEQUENCE: 15

Lys Ser Ser Gln Ser Leu Leu Asn Ser Gly Asn Gln Lys Asn Tyr Leu
1               5                   10                  15

Thr

<210> SEQ ID NO 16
<211> LENGTH: 17
<212> TYPE: PRT
<213> ORGANISM: Artificial Sequence
<220> FEATURE:
<223> OTHER INFORMATION: Synthetic Construct

<400> SEQUENCE: 16

Lys Ser Ser Gln Ser Leu Leu Gln Ser Gly Asn Gln Lys Asn Tyr Leu
1               5                   10                  15

Thr

<210> SEQ ID NO 17
<211> LENGTH: 17
<212> TYPE: PRT
<213> ORGANISM: Artificial Sequence
<220> FEATURE:
<223> OTHER INFORMATION: Synthetic Construct

<400> SEQUENCE: 17

Lys Ser Ser Gln Ser Leu Leu Ser Ser Gly Asn Gln Lys Asn Tyr Leu
1               5                   10                  15

Thr

<210> SEQ ID NO 18
<211> LENGTH: 7
<212> TYPE: PRT
<213> ORGANISM: Artificial Sequence
<220> FEATURE:
<223> OTHER INFORMATION: Synthetic Construct

<400> SEQUENCE: 18

Trp Thr Ser Thr Arg Glu Ser
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic Construct

```
<400> SEQUENCE: 19

Gln Asn Asp Tyr Thr Ser Pro Tyr Thr
1               5
```

ANTI-GLYCAN ANTIBODIES AND USES THEREOF

CROSS-REFERENCE TO RELATED APPLICATIONS

This application claims the benefit of U.S. Provisional Application 62/990,927, filed Mar. 17, 2020, U.S. Provisional Application 63/037,374, filed Jun. 10, 2020, and U.S. Provisional Application 63/074,956, filed Sep. 4, 2020, each of which is hereby incorporated by reference in its entirety.

FIELD

The present invention relates to anti-sialylated glycan antibodies including anti-sialyl Lewis A (sLeA) and anti-sialyl Lewis C (sLeC) antibodies and methods of using the same.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 203462000100SEQLIST.TXT, date recorded: Mar. 15, 2021, size: 14 KB).

BACKGROUND

Glycans are carbohydrate-based polymers that can be free or attached to proteins (glycoproteins) or lipids (glycolipids). The glycans of glycoproteins are known to be involved in immunity and inflammation, including sialylated glycans on glycoproteins. High expression of sLeA have been described in human pancreatic, colon and gastric cell lines as well as in adenocarcinomas of the colon, stomach and pancreas. Additionally, studies have shown sLeA upregulation in concert with CD44v6 in inflamed regions of human colon from patients with ulcerative colitis. Additionally, studies have shown a functional role for sLeA in mucosal inflammation which suggests that modulating sLeA may impact diseases including inflammatory bowel disease (e.g., Crohn's Disease or ulcerative colitis).

Aberrant glycosylation has also been described as one of the hallmarks of cancer and modulate immune responses. Similar to what has been observed on inflammatory bowel disease tissues, aberrant glycosylation of proteins leads to overexpression of tumor-associated carbohydrate antigens during malignant transformation. Studies have shown that tumor-associated carbohydrate antigens have contributed to various aspects of cancer development and progression, including proliferation, invasion, angiogenesis and metastasis (Fuster, Nat Rev Cancer, 5:526-42 (2005) and Dube, Nat Rev Drug Discovery, 4:477-88 (2005)).

One type of glycosylation are sialic acids and they are typically found to be terminating branches of N-glycans, O-glycans and glycosphingolipids. Within sialic acids, a variety of diversity are created through alpha linkages between the nine-carbon backbone and secondary diversity through modifications at these carbon positions. Examples of sialylated glycosylation found include sLeA, sLeC and sialyl Lewis X (glycan structure of each is found in Table 1).

These glycans are all examples of terminally sialylated glycans. While sLeC is the non-fucosylated precursor of sLeA, sLeX is a stereo isomer of sLeA. In general, sLeC is typically not found on normal human tissue, but found on murine tissues. Thus, antibodies that bind to both sLeA and sLeC would be useful for drug development especially for use in in vivo murine models of disease.

In general, antibodies that are suited for development as a pharmaceutical agent to treat disease and/or disorders have high specificity, selectivity and affinity. Thus, anti-glycan antibodies are typically not suited for development as pharmaceutical agents partially due to carbohydrate antigens have limited immunogenicity and the observed affinities of anti-carbohydrate antibodies are typically lower by factors of $10^3$-$10^5$ than antibodies specific for protein or peptide antigens (Ghassemi, Glycobiology, 25(9): 920-952 (September 2015)). The overall low binding of carbohydrates is usually accompanied by relative fast $k_{on}$ and $k_{off}$ rates, which results in an overall lower $K_D$ for anti-glycan antibodies.

The present invention addresses the need for an alternative antibody therapy that targets glycan epitopes for patients having disorders affecting the digestive system, including inflammatory bowel disease and cancers of the digestive system.

SUMMARY OF THE INVENTION

The present invention provides for antibodies or antigen binding portions thereof, comprising a variable region that bind to a carbohydrate antigen or a fragment thereof.

In one aspect, provided herein is an antibody, or an antigen-binding portion thereof, that binds to sialyl Lewis A (sLeA) and sialyl Lewis C (sLeC), wherein the binding affinity of such antibody or antigen-binding portion to sLeA is of $K_D$ of 60 μM or less and the binding affinity to sLeC is of $K_D$ 100 μM or less. In some embodiments, the antibody or antigen-binding portion does not bind to sialyl Lewis X (sLeX). In some embodiments, the antibody or antigen-binding portion is a humanized antibody or humanized antigen-binding portion.

In another aspect, provided herein is an antibody, or an antigen-binding portion thereof, that binds to sLeA and sLeC, comprising a heavy chain variable region and a light chain variable region, wherein the heavy chain variable region comprises a sequence having a 90-100% sequence identity to SEQ ID NO:1, SEQ ID NO: 2, or SEQ ID NO:3, and the light chain variable region comprises a sequence having a 90-100% sequence identity to SEQ ID NO: 4, SEQ ID NO: 5, SEQ ID NO: 6, or SEQ ID NO:7. In some embodiments, the antibody or antigen-binding portion does not bind to sLeX. In some embodiments, the heavy chain variable region comprises a CDR-H1 comprising the sequence of SEQ ID NO:12, a CDR-H2 comprising the sequence of SEQ ID NO:13, and a CDR-H3 comprising the sequence of SEQ ID NO:14; and the light chain variable region comprises a CDR-L1 comprising a sequence selected from the group consisting of SEQ ID NOs:15-17, a CDR-L2 comprising the sequence of SEQ ID NO:18, and a CDR-L3 comprising the sequence of SEQ ID NO:19. In some embodiments, the heavy chain variable region comprises the sequence of SEQ ID NO:3, and the light chain variable region comprises a sequence selected from the group consisting of SEQ ID Nos:5-8. In some embodiments, the heavy chain variable region comprises the sequence of SEQ ID NO:3, and the light chain variable region comprises the sequence of SEQ ID No:8. In some embodiments, the heavy chain variable region comprises the sequence of SEQ ID NO:4, and the light chain variable region comprises the sequence of SEQ ID NO:9 or 10.

In another aspect, provided herein is an antibody, or an antigen binding portion thereof, that binds to sLeA and sLeC, comprising a heavy chain variable region, wherein the heavy chain variable region comprises a sequence having a 90-100% sequence identity to SEQ ID NO: 3. In some embodiments, the antibody or antigen-binding portion comprises a light chain variable region, wherein the light chain variable region comprises a sequence having a 90-100% sequence identity to a sequence selected from the group consisting of SEQ ID Nos:5-11.

In another aspect, provided herein is an antibody, or an antigen binding portion thereof, that binds to sLeA and sLeC, comprising a heavy chain variable region and a light chain variable region, wherein the heavy chain variable region comprises a CDR-H1 comprising the sequence of SEQ ID NO:12, a CDR-H2 comprising the sequence of SEQ ID NO:13, and a CDR-H3 comprising the sequence of SEQ ID NO:14; and wherein the light chain variable region comprises a CDR-L1 comprising a sequence selected from the group consisting of SEQ ID NOs:15-17, a CDR-L2 comprising the sequence of SEQ ID NO:18, and a CDR-L3 comprising the sequence of SEQ ID NO:19. In some embodiments, the antibody or antigen-binding portion comprises a heavy chain variable region and a light chain variable region of a single antibody shown in Table 6.

In another aspect, provided herein is one or more polynucleotide(s) encoding the antibody or antigen-binding portion thereof according to any one of the above embodiments. In another aspect, provided herein is a vector comprising the one or more polynucleotide(s) according to any one of the above embodiments. In another aspect, provided herein is a host cell comprising the one or more polynucleotide(s) according to any one of the above embodiments or the vector according to any one of the above embodiments. In another aspect, provided herein is a method of producing an antibody, the method comprising culturing the host cell according to any one of the above embodiments such that the antibody is produced. In some embodiments, the method further comprises recovering the antibody from the host cell. In another aspect, provided herein is a pharmaceutical composition comprising the antibody or antigen-binding portion thereof according to any one of the above embodiments and a pharmaceutically acceptable carrier.

In another aspect, provided herein is a method of treating or ameliorating a symptom of a digestive disease or disorder wherein said method comprises administering to an individual with said digestive disease or disorder an effective amount of an antibody, antigen-binding portion, or pharmaceutical composition described herein. In some embodiments, the digestive disease or disorder is selected from inflammatory bowel disease, irritable bowel syndrome, pancreatic cancer, or colon cancer. In some embodiments, the digestive disease or disorder is inflammatory bowel disease. In some embodiments, the inflammatory bowel disease is Crohn's Disease or ulcerative colitis. In some embodiments, the individual is a human.

DETAILED DESCRIPTION OF THE INVENTION

As used herein, the articles "a" and "an" refer to one or more than one (i.e., at least one) of the grammatical object of the article. By way of example, "an element" means one element or more than one element.

The term "antibody" is intended to encompass antibodies, fragments, specified portions and variants thereof, including single chain antibodies and fragments thereof, derived from an antibody of the present invention. Antibodies include antibody fragments, antibody variants, monoclonal antibodies, polyclonal antibodies, and recombinant antibodies. Antibodies can be generated in mice, rats, rabbits, or humans.

The antibodies can be full-length or can comprise a fragment (or fragments) of the antibody having an antigen portion, including, but not limited to, Fab, Fab', and F(ab')$_2$, facb, pFc$^1$, Fd, dAb fragment, an isolated CDR, diabodies, triabodies, tetrabodies, linear antibodies, single-chain antibody molecules, bispecific and multi-specific antibodies formed from antibody fragments.

In some embodiments, the antibodies comprise all or a portion of a constant region of an antibody. The constant region is an isotype selected from IgA (e.g., IgA1 or IgA2), IgD, IgE, IgG (e.g., IgG1, IgG2, IgG3, or IgG4), IgM. As used herein, the "constant region" of an antibody includes the natural constant region, allotypes or natural variants, such as D356E and L358M or A431G in human IgG1. See, e.g., Jefferies and Lefranc, MAbs, 1(4): 332-338 (July-August 2009).

The term "monoclonal antibody" as used herein is not limited to antibodies produced through hybridoma technology. A monoclonal antibody is derived from a single clone, including any eukaryotic, prokaryotic, or phage clone, by any means available or known in the art. Monoclonal antibodies of the present invention can be prepared using a wide variety of techniques known in the art including the use of hybridoma, recombinant and phage display technologies, or a combination thereof.

The term "chimeric" antibody as used herein refers to an antibody having variable sequences derived from a non-human immunoglobulin, such as a rat or a mouse antibody, and a human immunoglobulin constant region, typically chosen from a human immunoglobulin template. Methods for producing chimeric antibodies are known in the art.

"Humanized" form of non-human (e.g., murine) antibodies are chimeric immunoglobulins that contain minimal sequences derived from non-human immunoglobulin. In general, a humanized antibody will comprise substantially all of at least one, and typically two, variable domains, in which all or substantially all of the CDR regions correspond to those of a non-human immunoglobulin and all or substantially all of the framework regions are those of a human immunoglobulin sequence. The humanized antibody can also comprise at least a portion of an immunoglobulin constant region (Fc), typically that or a human immunoglobulin consensus sequence. Methods of antibody humanization are known in the art.

An "effective amount" as used herein, refers to a dose of the antibody or pharmaceutical composition that is sufficient to reduce the symptoms and signs of diseases of the digestive system, including inflammatory bowel disease or cancers of the digestive system. Such symptoms of inflammatory bowel disease include diarrhea, weight loss, bloody diarrhea, bloody stool, pain, anemia, fatigue, rectal bleeding, and abdominal cramps. Symptoms of cancers of the digestive system include weight loss, pain and detectable mass, either clinically as a palpable mass or radiologically or through other imaging techniques. The term "effective amount" and "therapeutically effective amount" are used interchangeably. In some embodiments, an effective amount of a drug, compound, or pharmaceutical composition may or may not be achieved in conjunction with another drug, compound, or pharmaceutical composition. Thus, an "effective amount" may be considered in the context of administering one or more chemotherapeutic or other effective agents, and a single agent may be considered to be given in an effective amount if, in conjunction with one or more other agents, a desirable result may be or is achieved. While individual needs vary, determination of optimal ranges of effective amounts of each component is within the skill of the art. Typical dosages comprise 0.1 to 100 mg/kg/body weight. The preferred dosages comprise 1 to 100 mg/kg/body weight. The most preferred dosages comprise 10 to 100 mg/kg/body weight.

The term "subject" or "individual" can refer to a vertebrate having a disease of the digestive system, such as a vertebrate having inflammatory bowel disease or cancer of the digestive system. Subjects include all warm-blooded animals, such as mammals, such as a rodent, preferably a primate or non-human primate, and more preferably, a human. The term subject includes domesticated animals, such as cats, dogs, etc., livestock (for example, cattle, horses, pigs, sheep, goats, etc.), and laboratory animals (for example, mouse, rabbit, rat, gerbil, guinea pig, etc.). Thus, veterinary uses and medical or pharmaceutical formulations are contemplated herein.

One of skill in the art will recognize that antibodies are "modular" in nature. Throughout the disclosure, various specific embodiments of the various "modules" composing the antibodies of the present invention are described. As specific non-limiting examples, various embodiments of variable heavy chain CDRs, variable heavy chains, variable light chain CDRs, and variable light chains are described. It is intended that all of the specific embodiments may be combined with each other as though each specific combination were explicitly described individually.

Humanized antibodies of the present invention can comprise a heavy chain variable region from Table 1 below and additionally, can comprise a light chain variable region from Table 2 below. Such variable regions can be incorporated into a human IgG1 backbone using methods that are well known in the art.

TABLE 1

Heavy Chain Variable Region Sequences

| HvCh1 | SEQ ID NO: 1 | EVQLVESGGGLVQPGGSLRLSCAASGFTFSTNAMSWVRQAPGKGLEWVSRLRPKSDNYATYYADSVKGRFTISRDNSKNTLYLQMNSLRAEDTAVYYCAKGTGFWGQGTTVTVSS |
| HvCh2 | SEQ ID NO: 2 | EVQLVESGGGLVQPGGSLRLSCAASGFTFSTNAMSWVRQAPGKGLEWVARLRPKSDNYATYYADSVKGRFTISRDNSKNTLYLQMNSLRAEDTAVYYCVTGTGFWGQGTTLTVSS |
| HvCh3 | SEQ ID NO: 3 | EVQLVESGGGLVQPGGSLRLSCAASGFTFSTNAMSWVRQAPGKGLEWVARLRPKSDNYATYYADSVKGRFTISRDDSKNTLYLQMNSLRAEDTAVYYCVTGTGFWGQGTTLTVSS |
| HvCh4 | SEQ ID NO: 4 | EVQLVESGGGLVQPGGSLRLSCAASGFTFSTNAMSWVRQAPGKGLEWVARLRPKSDNYATYYADSVKGRFTISRDDSTSTLYLQMNSLRAEDTAVYYCVTGTGFWGQGTTLTVSS |

TABLE 2

Light Chain Variable Region Sequences

| LiCh1 | SEQ ID NO: 5 | DIVMTQSPDSLAVSLGERATINCKSSQSLLNSGNQKNYLTWYQQKPGQPPKLLIYWTSTRESGVPDRFSGSGSGTDFTLTISSLQAEDVAVYYCQNDYTSPYTFGQGTKLEIK |
| LiCh2 | SEQ ID NO: 6 | DIVMTQSPDSLAVSLGERVTMNCKSSQSLLNSGNQKNYLTWYQQKPGQPPKLLIYWTSTRESGVPDRFSGSGSGTDFTLTISSVQAEDVAVYYCQNDYTSPYTFGQGTKLEIK |
| LiCh3 | SEQ ID NO: 7 | DIVMTQSPDSLAVSLGERATINCKSSQSLLNSGNQKNYLTWYQQKPGQPPKLLFYWTSTRESGVPDRFSGSGSGTDFTLTISSLQAEDVAVYYCQNDYTSPYTFGQGTKLEIK |
| LiCh4 | SEQ ID NO: 8 | DIVMTQSPDSLAVSLGERVTMNCKSSQSLLNSGNQKNYLTWYQQKPGQPPKLLFYWTSTRES GVPDRFSGSGSGTDFTLTISSVQAEDVAVYYCQNDYTSPYTFGQGTKLEIK |
| LiCh5 | SEQ ID NO: 9 | DIVMTQSPDSLAVSLGERVTMNCKSSQSLLNSGNQKNYLTWYQQKPGQPPKLLFYWTSTRESGVPDRFSGSGSGTDFTLTISSVQAEDLAVYYCQNDYTSPYTFGQGTKLEIK |
| LiCh6 | SEQ ID NO: 10 | DIVMTQSPDSLAVSLGERVTMNCKSSQSLLQSGNQKNYLTWYQQKPGQPPKLLFYWTSTRESGVPDRFSGSGSGTDFTLTISSVQAEDLAVYYCQNDYTSPYTFGQGTKLEIK |
| LiCh7 | SEQ ID NO: 11 | DIVMTQSPDSLAVSLGERVTMNCKSSQSLLSSGNQKNYLTWYQQKPGQPPKLLFYWTSTRESGVPDRFSGSGSGTDFTLTISSVQAEDLAVYYCQNDYTSPYTFGQGTKLEIK |

In other embodiments, the humanized antibodies of the present invention can comprise heavy and light chain CDR sequences selected from Tables 3 and 4 below:

TABLE 3

Heavy Chain CDR sequences

| H-CDR1 | SEQ ID NO: 12 | GFTFSTNAMS |
| H-CDR2 | SEQ ID NO: 13 | RLRPKSDNYATY |
| H-CDR3 | SEQ ID NO: 14 | VTGTGF |

TABLE 4

| | Light Chain CDR sequences | |
|---|---|---|
| L-CDR1 | SEQ ID NO: 15 | KSSQSLLNSGNQKNYLT |
| L-CDR1B | SEQ ID NO: 16 | KSSQSLLQSGNQKNYLT |
| L-CDR1C | SEQ ID NO: 17 | KSSQSLLSSGNQKNYLT |
| L-CDR2 | SEQ ID NO: 18 | WTSTRES |
| L-CDR3 | SEQ ID NO: 19 | QNDYTSPYT |

The present invention includes antibodies and fragments that specifically binds to sLeA and sLeC, but not sialyl Lewis X (sLeX), compositions comprising antibodies, polynucleotides encoding anti-sLeA/sLeC, but not sLeX antibodies, polynucleotides encoding such antibodies, methods and compositions useful for making such antibodies and binding fragments, and various methods using the same. Glycan structures of sLeA, sLeC, and sLeX are shown in Table 5 below.

TABLE 5

Glycan structure of sialyl Lewis A, sialyl Lewis C, and sialyl Lewis X

| Glycan name | Glycan structure |
|---|---|
| sialyl Lewis A (sLeA) | NeuAc α2,3 Galβ1,3 [Fucα1,4] GlcNAc |
| sialyl Lewis C (sLeC) | NeuAc α2,3 Galβ1,3 GlcNAc |
| sialyl Lewis X (sLeX) | NeuAc α2,3 Galβ1,4 [Fucα1,3] GlcNAc |

Antibodies against carbohydrate/glycans can be unsuitable for pharmaceutical development because of its generally lower binding affinity. Methods for determining binding affinities for antibodies are known in the art. Generally, the binding affinity to a particular target or substrate is determined by the relationship between the on rate ($k_a$ ($M^{-1}s^{-1}$)) and off rate ($k_d$ ($s^{-1}$)) to produce an equilibrium dissociation constant ($K_D$). The lower the $K_D$, the higher the affinity. Examples of methods for determining antibody affinity include assays utilizing the Octet system (Fortébio) or the Biacore system (GE Healthcare) or other systems instrumentation that determine association and dissociation constants. Accordingly, the present invention comprises antibodies having binding affinity to sLeA of a $K_D$ of about 500 µM or less and binding affinity to sLeC of a $K_D$ of about 500 µM or less, and no binding to sLeX. In non-limiting examples, antibodies of the present invention comprise a binding affinity to sLeA of a $K_D$ of 100 µM or less, 90 µM or less, 80 µM or less, 70 µM or less, 60 µM or less, 50 µM or less, 40 µM or less, 30 µM or less, 20 µM or less, 10 µM or less, 1 µM or less, or 0.1 µM or less, and a binding affinity to sLeC of a $K_D$ of 100 µM or less, 90 µM or less, 80 µM or less, 70 µM or less, 60 µM or less, 50 µM or less, 40 µM or less, 30 µM or less, 20 µM or less, 10 µM or less, 1 µM or less, or 0.1 µM or less, and no binding to sLeX. In one embodiment, antibodies that are useful in the present invention have a binding affinity to their glycan targets of a $K_D$ of 41 µM or less for sLeA and a $K_D$ of 70 µM or less for sLeC and no binding to sialyl Lewis X (sLeX). In some embodiments, an antibody of the present disclosure does not bind to a particular target (e.g., sLeX) if the binding affinity of the antibody to the target is of a $K_D$ of about 1 mM or higher.

Antibodies of the present invention may also be used in methods of aiding diagnosis of disease, such as diagnosis of cancer in an individual. Such cancers include cancers of the digestive system such as pancreatic or colon cancer. Such methods include using the antibodies of the present invention to determine the level of sLeA and/or sLeC binding in an individual or specific tissue in an individual. As used herein, methods for "aiding diagnosis" means that these methods assist in making a clinical determination regarding the classification, or nature, or cancer, and may or may not be conclusive with respect to the definitive diagnosis. Accordingly, a method of aiding diagnosis of cancer can comprise the step of detecting the level of sLeA and/or sLeC in a biological sample from the individual and/or determining the level of sLeA and/or sLeC in the sample. Antibodies recognizing the epitope or a portion thereof may also be used to create diagnostic immunoassays for detecting antigenic determinant released in the bodily fluids, including but not limited to blood, saliva, urine, pulmonary fluid, or ascites fluid. Similarly, such immunoassays using the antibodies of the present invention may be used to monitor the efficacy of treatment and/or disease remission. In such instances, the presence and/or levels of the antigenic determinant reactive to the antibody of the present invention may be useful as a biomarker in order to monitor disease activity and/or progression.

In some embodiments, an antibody of the present disclosure may also be used in a method of detecting the presence and/or measuring the level of sLeA and/or sLeC in an individual or specific tissue in an individual.

Certain aspects of the present disclosure relate to polynucleotides (e.g., isolated polynucleotides) and/or vectors (e.g., expression vectors) encoding an antibody of the present disclosure, as well as host cells (e.g., isolated host cells) comprising the polynucleotides or vectors. In some embodiments, the host cell is a prokaryotic host cell, such as a bacterial host cell (e.g., *E. coli*). Suitable prokaryotic host cells include without limitation eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, etc. In some embodiments, the host cell is a eukaryotic host cell such as yeast, fungi, insect, plant, animal, human, or nucleated cells from other multicellular organisms. For example, filamentous fungi or yeast are suitable cloning or expression hosts for antibody-encoding vectors. *Saccharomyces cerevisiae*, or common baker's yeast, is the most commonly used among lower eukaryotic host microorganisms. Suitable host cells for the expression of glycosylated antibody are also derived from multicellular organisms (invertebrates and vertebrates). Examples of invertebrate cells include plant and insect cells. Examples of vertebrate or mammalian cells include, e.g., monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; a human hepatoma line (Hep G2); Chinese hamster ovary (CHO)

cells, including DHFR− CHO cells (Urlaub et al., *Proc. Natl. Acad. Sci. USA* 77:4216 (1980)); and myeloma cell lines such as NSO and Sp2/0.

Other aspects of the present disclosure relate to methods of production using a host cell of the present disclosure. Antibodies or antigen-binding portions thereof can be produced using recombinant methods. For recombinant production of an antibody or antigen-binding portion, nucleic acid encoding the antibody/portion is isolated and inserted into a vector for further cloning (amplification of the DNA) or for expression. DNA encoding the antibody can be isolated and sequenced using conventional procedures (e.g., by using oligonucleotide probes that are capable of binding specifically to genes encoding the heavy and light chains of the antibody). The vector components generally include, but are not limited to, one or more of the following: a signal sequence, an origin of replication, one or more marker genes, an enhancer element, a promoter, and a transcription termination sequence.

Antibodies of the present invention may be used for therapeutic purposes in individuals with diseases or disorders of the digestive system. Such diseases include but are not limited to inflammatory bowel disease (e.g., Crohn's Disease and ulcerative colitis), irritable bowel syndrome, and cancers of the digestive system including pancreatic and colon cancer.

In some embodiments, the antibodies of the present invention may be used alone for the treatment or ameliorating one or more disease symptom. In other embodiments, the antibodies of the present invention may be used in combination with other therapeutics or pharmaceutical agents to treat or ameliorate one or more disease symptom.

Various formulations of antibodies of the present invention or fragments thereof may be used for administration. In some embodiments, the antibodies of the present invention or fragments thereof may be administered neat. In addition to the pharmacologically active agent, the compositions of the present invention may contain suitable pharmaceutically acceptable carriers comprising excipients and auxiliaries that are well known in the art and are relatively inert substances that facilitate administration of a pharmacologically effective substance or which facilitate processing of the active compounds into preparations that can be used pharmaceutically for delivery to the site of action. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers.

Suitable formulations for parenteral administration include aqueous solutions of the active compounds in water-soluble form, for example, water-soluble salts. In addition, suspensions of the active compounds as appropriate for oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances that increase the viscosity of the suspension and include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulation may be used simultaneously to achieve systemic administration of the active ingredient. Excipients as well as formulations for parenteral and nonparenteral drug delivery are set forth in Remington, The Science and Practice of Pharmacy 20th Ed. Mack Publishing (2000).

Suitable formulations for oral administration include hard or soft gelatin capsules, pills, tablets, including coated tablets, elixirs, suspensions, syrups or inhalations and controlled release forms thereof.

Generally, these agents are formulated for administration by injection (e.g., intraperitoneally, intravenously, subcutaneously, intramuscularly, etc.), although other forms of administration (e.g., oral, mucosal, etc) can be also used. Accordingly, antibodies of the present invention are preferably combined with pharmaceutically acceptable vehicles such as saline, Ringer's solution, dextrose solution, and the like.

The particular dosage regimen, i.e., dose, timing and repetition, will depend on the particular individual and that individual's medical history. Generally, a dose of at least about 0.1 mg/kg body weight, or more preferably, at least about 1 mg/kg body weight, or at least about 5 mg/kg body weight, even more preferably at least about 10 mg/kg body weight or at least about 20 mg/kg body weight is administered.

In some embodiments, one or more doses of the antibodies of the present invention or fragments thereof will be administered during a course of treatment. Empirical considerations, such as half-life, generally will contribute to the determination of the dosage. Antibodies, which are compatible with the human immune system, such as humanized antibodies or fully human antibodies ma y be used to prolong half-life of the antibody and prevent the antibody being attacked by the host's immune system. Frequency of administration may be determined and adjusted over the course of therapy, and may be based on the reduction of one of more clinical symptoms of the disease. Alternatively, sustained continuous release formulations of the antibodies of the present invention may be appropriate. Various formulations and devices for achieving sustained release are known in the art.

The following examples are provided to illustrate, but not to limit the invention.

EXAMPLES

Example 1. Generation of Humanized Antibody Clones

Humanized antibodies, with a heavy chain variable region comprising one of the heavy chain variable regions from Table 1 above and a light chain variable region comprising one of the light chain variable regions from Table 2 above were synthesized and incorporated into an IgG1 backbone. Heavy and light chain variable region pairs that were incorporated into an IgG1 backbone and synthesized were the ones in the Table 6 below.

TABLE 6

Humanized Antibody Clones

| Humanized Antibody Clone | Heavy Chain Variable Region | SEQ ID NO: | Light Chain Variable Region | SEQ ID NO: |
|---|---|---|---|---|
| 4764 | HvCh1 | 1 | LiCh1 | 5 |
| 4765 | HvCh2 | 2 | LiCh1 | 5 |
| 4766 | HvCh2 | 2 | LiCh2 | 6 |
| 4767 | HvCh2 | 2 | LiCh3 | 7 |
| 4768 | HvCh2 | 2 | LiCh4 | 8 |

TABLE 6-continued

Humanized Antibody Clones

| Humanized Antibody Clone | Heavy Chain Variable Region | SEQ ID NO: | Light Chain Variable Region | SEQ ID NO: |
|---|---|---|---|---|
| 4769 | HvCh3 | 3 | LiCh1 | 5 |
| 4770 | HvCh3 | 3 | LiCh2 | 6 |
| 4771 | HvCh3 | 3 | LiCh3 | 7 |
| 4772 | HvCh3 | 3 | LiCh4 | 8 |

Humanized antibodies with the above combinations of heavy and light chain variable region pairs were produced by transfecting the plasmids into mammalian cells and purified using affinity chromatography.

Of the nine humanized antibody clones in Table 6, two antibody clones (4764 and 4767) showed weak expression, resulting in less than 1 mg of antibody after purification. The production levels for these two clones were deemed too low for practical production cell line optimization. The remaining seven clones were then screened for binding affinity to sLeA, sLeC and sLeX.

Example 2. Binding Affinity to Sialyl Lewis a (sLeA) and Sialyl Lewis C (sLeC)

An in vitro evaluation of the binding affinity to sLeA and sLeC of the humanized antibodies from Example 1 were performed using a Biocore T100 SPR biosensor using a CM7 sensor chip with PBS-p (0.005% Tween-20) running buffer at 25 degrees Celsius. The antibodies were couples to ~30,000 RU at 50 ug/ml in 10 mM NaAcetate pH 5.0 over an NHS/EDC activated surface. A reference surface was activated and blocked to serve as a control. Carbohydrate samples (sLeA, sLeC and sialyl Lewis X (all from Dextra Labs)) were dissolved in PBS-p running buffer up to a stock concentration of 10 mM. Each was then prepared in a 2-fold dilution series up to 300 μM and each concentration series was tested over the antibody surfaces. Response data were processed by subtracting the responses from the reference surfaces as well as a buffer injection. Binding constants were determined at 25 degrees Celsius.

We tested a murine antibody (GM35) described in Brazil, J Immunol 191:4804-4817 (2013) for binding affinities for sLeA, sLeC and sLeX using the methods described above. The results for this antibody did not show binding to sLeX, had a $K_D$ for sLeA of 41.5 μM to 46.8 μM, and a $K_D$ for sLeC of 68.8 μM to 78.2 Comparatively, another antibody that was tested was NS19-9 (Dako, Carpenteria, Calif.), an antibody known to bind to sLeA, which did not show binding to sLeX, had a $K_D$ for sLeA of 39.5 μM, and a $K_D$ for sLeC of 1.5 mM.

Example 3. Binding Affinity to Sialyl Lewis a (sLeA) and Sialyl Lewis C (sLeC) for Humanized Antibody Clones Seven of the humanized antibody clones from Example 1 were tested for binding affinity to sLeA, sLeC and sLeA. Methods used were similar to those described in Example 2 above, except with sLeX only at one concentration of 300 μM. Mean binding $K_D$ for sLeA and sLeC for each of the seven humanized antibody clones are shown in Table 7 below.

TABLE 7

Binding Affinity for Humanized Antibody Clones

| Humanized Antibody Clone | sLeA Mean $K_D$ in μM | sLeC Mean $K_D$ in μM |
|---|---|---|
| 4765 | 731.7 | 306.3 |
| 4766 | 620.7 | 538.0 |
| 4768 | 552.0 | 460.0 |
| 4769 | 81.3 | 103.7 |
| 4770 | 69.1 | 93.2 |
| 4771 | 59.2 | 85.4 |
| 4772 | 48.3 | 77.1 |

None of the above antibody clones showed binding to sLeX in three independent runs at a concentration of 300 μM of the carbohydrate. From the above binding affinity data, humanized antibody clones with HvCh3 variable regions had the highest affinity for both sLeA and sLeC.

Example 4. In Vitro Wound Healing Activity

Figure 1A:
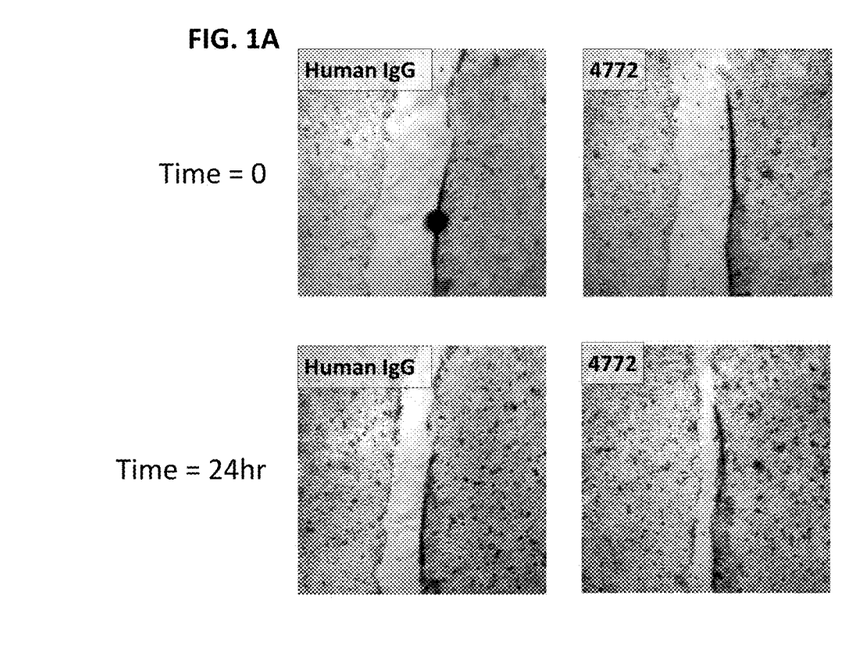
FIG. 1A are microscopic images from in vitro scratch wound assays using T84 cells at time 0 and 24 hour after treatment with either human IgG control or antibody clone 4772.
Figure 1B:
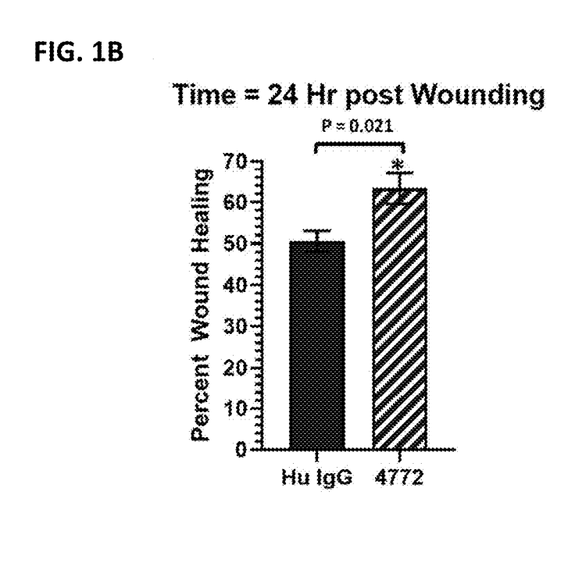
FIG. 1B illustrates the difference in wound healing activity observed after 24 hours of treatment.

The wound healing mechanism of action of the humanized antibodies were tested in an in vitro scratch wound assay. Human colon epithelial cells, T84 (CCL-248, ATCC, Manassas, Va.) were grown to confluency in 6-well plates. A scratch wound was made in each condition using a pipette tip and the cells were treated with either 10 ug/ml human IgG (hIgG) control (Sigma-Aldrich) or 10 ug/ml humanized antibody of Example 3 above. Wound healing activity was measured after 24 hours after treatment by visual inspection and measurement of size of the scratch wound by ImageJ based image analysis. The humanized antibody showed greater wound healing activity compared to hIgG control. As a non-limiting example, the wound healing activity of one of the humanized antibody clones of Example 3, clone 4772, is shown in FIGS. 1A-1B. The increased in wound healing activity seen in FIGS. 1A and 1B shows that humanized antibodies of Example 3, including antibody clone 4772, may be efficacious in the treatment of disorders of the digestive system, including inflammatory bowel disease.

Example 5. In Vivo Efficacy in Acute Model of DSS-Induced Colitis

Efficacy of antibody clone 4772 was tested in an in vivo murine acute model of dextran sodium sulfate (DSS)-induced colitis. On Study Day −1, all animals were randomized by body weight. Animals with a body weight between 18-22 g will be enrolled into the study. Starting on Study Day 0, all 10 week old male C57BL/6 mice enrolled in the study that do not belong to the "naïve" group received 2.5% Dextran Sodium Sulfate (DSS) dissolved in sterile water ad libitum for 7 days. DSS water was refreshed on study day 3. On study day 7 after all measurements are completed, all animals were switched to water only for drinking. Mice in the "naïve" group received only acidified water ad libitum and no test article treatment.

Animals receiving antibody clone 4772 or human IgG were injected on two separate days via intraperitoneal (IP) injections with the appropriate drug on study day 1 and 3 at 10 mg/kg body weight (4772) or 25 mg/kg body weight (human IgG). Mice in group designated to receive PBS received PBS IP injections at day 1 and day 3.

Figure 2A:
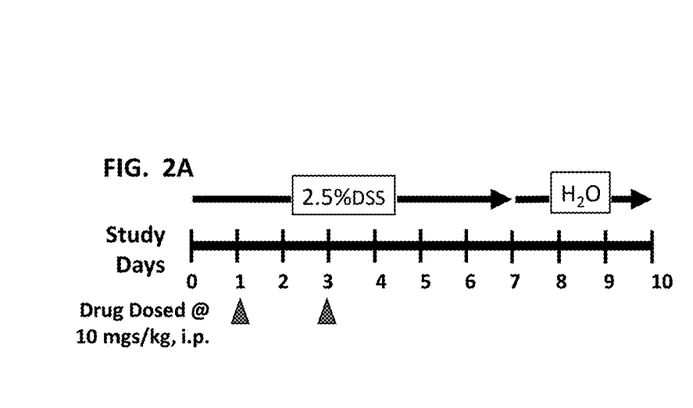
FIG. 2A is a schematic representation of the treatment protocol of an acute DSS-induced model of colitis.
Figure 2B:
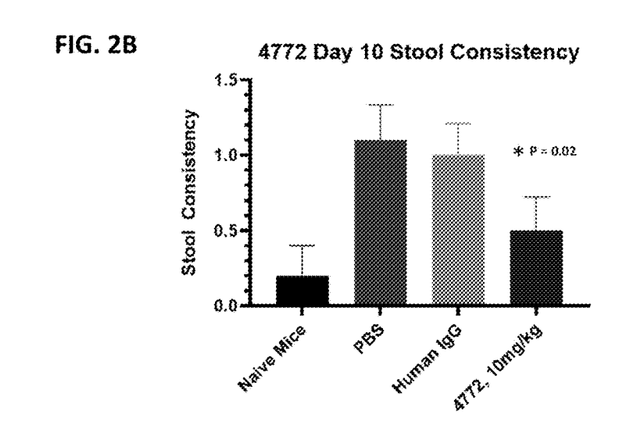
FIG. 2B illustrates Day 10 stool consistency of mice that are naïve (untreated, no DSS), PBS treated (dosed on Day 1 and Day 3, DSS), human IgG treated (dosed on Day 1 and Day 3, DSS) and antibody clone 4772 treated (dosed on Day 1 and Day 3, DSS).
Figure 2C:
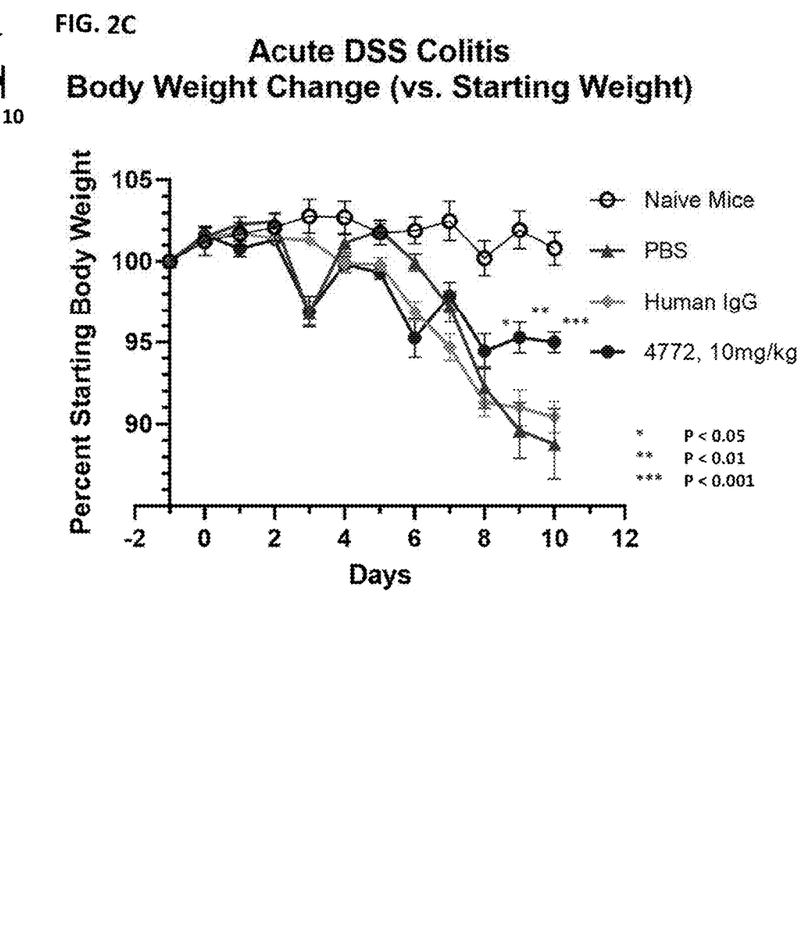
FIG. 2C illustrates body weight change as expressed as percent of starting body weight for mice that are naïve (untreated, no DSS), PBS treated (dosed on Day 1 and Day 3, DSS), human IgG treated (dosed on Day 1 and Day 3, DSS) and antibody clone 4772 treated (dosed on Day 1 and Day 3, DSS).

Body weights were measured daily starting from study day −1 with stool consistency scoring performed on days 0, 2, 4, 6, 8, 9, 10, and 13. Results from this study are illustrated in FIGS. 2A-2E. FIG. 2A shows a schematic representation of the methods of the study. FIG. 2B illustrates the results of the stool consistency measured on day 10. As shown, the mice that received antibody clone 4772 had better stool consistency (lower on the y-axis) compared to PBS and hIgG control. Similarly, in FIG. 2B, mice treated with antibody clone 4772 had less body weight loss compared to PBS and hIgG control. Stool consistency and body weight loss are two factors that are indicative of symptoms of diseases of the digestive system, including inflammatory bowel disease. These data show that humanized antibodies of Example 3, including antibody clone 4772, may be efficacious in the treatment of disorders of the digestive system, including inflammatory bowel disease.

Figure 2D:
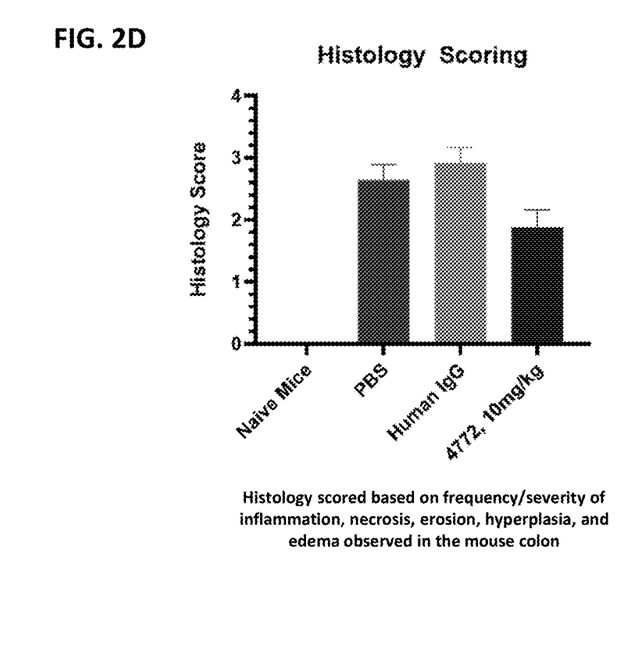
FIG. 2D illustrates severity of inflammation by histology of mouse intestinal tissue after terminal sacrifice for naïve mice (untreated, no DSS), PBS treated mice (dosed on Day 1 and Day 3, DSS), human IgG treated mice (dosed on Day 1 and Day 3, DSS) and antibody clone 4772 treated mice (dosed on Day 1 and Day 3, DSS).
Figure 2E:
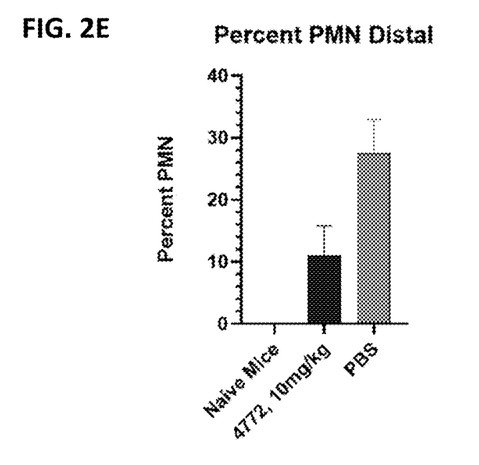
FIG. 2E illustrates the percent polymorphonuclear cells (PMNs) present in distal colon sections of mouse tissue after terminal sacrifice for naïve mice (untreated, no DSS), PBS treated mice (dosed on Day 1 and Day 3, DSS) and 4772 treated mice (dosed on Day 1 and Day 3, DSS).

Intestinal tissue samples collected after terminal sacrifice were scored for severity of inflammation (necrosis, erosion, hyperplasia, percent polymorphonuclear neutrophil (PMNs) infiltrates, and edema observed in the colon tissue. As shown in FIG. 2D, the mice that received antibody clone 4772 showed less signs of inflammation compared to PBS and hIgG control. Additionally, mice that received antibody clone 4772 had more than 50% less PMN infiltrates in the distal colon compared to mice treated with PBS (FIG. 2E). These data show that humanized antibodies of Example 3, including antibody clone 4772 may reduce inflammation intestinal tissues after DSS-induced wounding and may be efficacious in the treatment of disorders of the digestive system, including inflammatory bowel disease.

```
SEQUENCE LISTING
Amino acid sequence of HvCh1
                                    SEQ ID NO: 1
EVQLVESGGGLVQPGGSLRLSCAASGFTFSTNAMSWVRQAPGKGLEWVSRL

RPKSDNYATYYADSVKGRFTISRDNSKNTLYLQMNSLRAEDTAVYYCAKGT

GFWGQGTTVTVSS;

Amino acid sequence of HvCh2
                                    SEQ ID NO: 2
EVQLVESGGGLVQPGGSLRLSCAASGFTFSTNAMSWVRQAPGKGLEWVARL

RPKSDNYATYYADSVKGRFTISRDNSKNTLYLQMNSLRAEDTAVYYCVTGT

GFWGQGTTLTVSS;

Amino acid sequence of HvCh3
                                    SEQ ID NO: 3
EVQLVESGGGLVQPGGSLRLSCAASGFTFSTNAMSWVRQAPGKGLEWVARL

RPKSDNYATYYADSVKGRFTISRDDSKNTLYLQMNSLRAEDTAVYYCVTGT

GFWGQGTTLTVSS;

Amino acid sequence of HvCh4
                                    SEQ ID NO: 4
EVQLVESGGGLVQPGGSLRLSCAASGFTFSTNAMSWVRQAPGKGLEWVARL

RPKSDNYATYYADSVKGRFTISRDDSTSTLYLQMNSLRAEDTAVYYCVTGT

GFWGQGTTLTVSS;

Amino acid sequence of LiCh1
                                    SEQ ID NO: 5
DIVMTQSPDSLAVSLGERATINCKSSQSLLNSGNQKNYLTWYQQKPGQPPK

LLIYWTSTRESGVPDRFSGSGSGTDFTLTISSLQAEDVAVYYCQNDYTSPY

TFGQGTKLEIK;

Amino acid sequence of LiCh2
                                    SEQ ID NO: 6
DIVMTQSPDSLAVSLGERVTMNCKSSQSLLNSGNQKNYLTWYQQKPGQPPK

LLIYWTSTRESGVPDRFSGSGSGTDFTLTISSVQAEDVAVYYCQNDYTSPY

TFGQGTKLEIK;

Amino acid sequence of LiCh3
                                    SEQ ID NO: 7
DIVMTQSPDSLAVSLGERATINCKSSQSLLNSGNQKNYLTWYQQKPGQPPK

LLFYWTSTRESGVPDRFSGSGSGTDFTLTISSLQAEDVAVYYCQNDYTSPY

TFGQGTKLEIK;

Amino acid sequence of LiCh4
                                    SEQ ID NO: 8
DIVMTQSPDSLAVSLGERVTMNCKSSQSLLNSGNQKNYLTWYQQKPGQPPK

LLFYWTSTRESGVPDRFSGSGSGTDFTLTISSVQAEDVAVYYCQNDYTSPY

TFGQGTKLEIK;

Amino acid sequence of LiCh5
                                    SEQ ID NO: 9
DIVMTQSPDSLAVSLGERVTMNCKSSQSLLNSGNQKNYLTWYQQKPGQPPK

LLFYWTSTRESGVPDRFSGSGSGTDFTLTISSVQAEDLAVYYCQNDYTSPY

TFGQGTKLEIK;

Amino acid sequence of LiCh6
                                    SEQ ID NO: 10
DIVMTQSPDSLAVSLGERVTMNCKSSQSLLQSGNQKNYLTWYQQKPGQPPK

LLFYWTSTRESGVPDRFSGSGSGTDFTLTISSVQAEDLAVYYCQNDYTSPY

TFGQGTKLEIK;

Amino acid sequence of LiCh7
                                    SEQ ID NO: 11
DIVMTQSPDSLAVSLGERVTMNCKSSQSLLSSGNQKNYLTWYQQKPGQPPK

LLFYWTSTRESGVPDRFSGSGSGTDFTLTISSVQAEDLAVYYCQNDYTSPY

TFGQGTKLEIK;

Amino acid sequence of heavy chain CDR-1
                                    SEQ ID NO: 12
GFTFSTNAMS;

Amino acid sequence of heavy chain CDR-2
                                    SEQ ID NO: 13
RLRPKSDNYATY;

Amino acid sequence of heavy chain CDR-3
                                    SEQ ID NO: 14
VTGTGF;

Amino acid sequence of light chain CDR-1
                                    SEQ ID NO: 15
KSSQSLLNSGNQKNYLT;

Amino acid sequence of light chain CDR-1B
                                    SEQ ID NO: 16
KSSQSLLQSGNQKNYLT;

Amino acid sequence of light chain CDR-1C
                                    SEQ ID NO: 17
KSSQSLLSSGNQKNYLT;

Amino acid sequence of light chain CDR-2
                                    SEQ ID NO: 18
WTSTRES;

Amino acid sequence of light chain CDR-3
                                    SEQ ID NO: 19
QNDYTSPYT;
```

What is claimed is:

1. An antibody, or an antigen-binding portion thereof, that binds to sialyl Lewis A (sLeA) and sialyl Lewis C (sLeC), wherein the antibody or antigen-binding portion comprises a heavy chain variable region and a light chain variable region, wherein the heavy chain variable region comprises a CDR-H1 comprising the sequence of SEQ ID NO:12, a CDR-H2 comprising the sequence of SEQ ID NO:13, and a CDR-H3 comprising the sequence of SEQ ID NO:14; and wherein the light chain variable region comprises a CDR-L1 comprising a sequence selected from the group consisting of SEQ ID NOs:15-17, a CDR-L2 comprising the sequence of SEQ ID NO:18, and a CDR-L3 comprising the sequence of SEQ ID NO:19.

2. The antibody or antigen-binding portion of claim 1, wherein the antibody or antigen-binding portion does not bind to sialyl Lewis X (sLeX).

3. The antibody or antigen-binding portion of claim 1, wherein the antibody or antigen-binding portion is a humanized antibody or humanized antigen-binding portion.

4. The antibody or antigen-binding portion of claim 1, wherein:
   the heavy chain variable region comprises a sequence having a 90-100% sequence identity to SEQ ID NO: 2, SEQ ID NO:3, or SEQ ID NO: 4; and
   the light chain variable region comprises a sequence having a 90-100% sequence identity to SEQ ID NO: 5, SEQ ID NO: 6, SEQ ID NO: 7, SEQ ID NO:8, SEQ ID NO: 9, SEQ ID NO: 10, or SEQ ID NO: 11.

5. The antibody or antigen-binding portion of claim 4, wherein the heavy chain variable region comprises the sequence of SEQ ID NO:3, and wherein the light chain variable region comprises a sequence selected from the group consisting of SEQ ID Nos:5-8.

6. The antibody or antigen-binding portion of claim 5, wherein the light chain variable region comprises the sequence of SEQ ID NO:8.

7. The antibody or antigen-binding portion of claim 4, wherein the heavy chain variable region comprises the sequence of SEQ ID NO:4, and wherein the light chain variable region comprises a sequence selected from the group consisting of SEQ ID Nos:9-10.

8. The antibody or antigen-binding portion of claim 1, wherein the heavy chain variable region comprises a sequence having a 90-100% sequence identity to SEQ ID NO: 3.

9. The antibody or antigen-binding portion of claim 8, wherein the antibody or antigen-binding portion comprises a light chain variable region, wherein the light chain variable region comprises a sequence having a 90-100% sequence identity to a sequence selected from the group consisting of SEQ ID Nos:5-11.

10. A polynucleotide encoding the antibody or antigen-binding portion thereof of claim 1.

11. A vector comprising the polynucleotide of claim 10.

12. A host cell comprising the polynucleotide of claim 10.

13. A host cell comprising the vector of claim 11.

14. A method of producing an antibody, the method comprising culturing the host cell of claim 12 such that the antibody is produced.

15. A method of producing an antibody, the method comprising culturing the host cell of claim 13 such that the antibody is produced.

16. The method of claim 14, further comprising recovering the antibody from the host cell.

17. A pharmaceutical composition comprising the antibody or antigen-binding portion thereof of claim 1 and a pharmaceutically acceptable carrier.

18. A method of treating or ameliorating a symptom of a digestive disease or disorder wherein said method comprises administering to an individual with said digestive disease or disorder an effective amount of the antibody or antigen-binding portion of claim 1.

19. A method of treating or ameliorating a symptom of a digestive disease or disorder wherein said method comprises administering to an individual with said digestive disease or disorder an effective amount of the pharmaceutical composition of claim 17.

20. The method of claim 18, wherein the digestive disease or disorder is selected from the group consisting of inflammatory bowel disease, irritable bowel syndrome, pancreatic cancer and colon cancer.

21. The method of claim 20, wherein the digestive disease or disorder is inflammatory bowel disease.

22. The method of claim 21, wherein the inflammatory bowel disease is Crohn's Disease or ulcerative colitis.

23. The method of claim 18, wherein the individual is a human.

24. The antibody or antigen-binding portion of claim 1, wherein the heavy chain variable region comprises a CDR-H1 comprising the sequence of SEQ ID NO:12, a CDR-H2 comprising the sequence of SEQ ID NO:13, and a CDR-H3 comprising the sequence of SEQ ID NO:14; and wherein the light chain variable region comprises a CDR-L1 comprising the sequence of SEQ ID NO:15, a CDR-L2 comprising the sequence of SEQ ID NO:18, and a CDR-L3 comprising the sequence of SEQ ID NO:19.

25. The antibody or antigen-binding portion of claim 1, wherein the heavy chain variable region comprises a CDR-H1 comprising the sequence of SEQ ID NO:12, a CDR-H2 comprising the sequence of SEQ ID NO:13, and a CDR-H3 comprising the sequence of SEQ ID NO:14; and wherein the light chain variable region comprises a CDR-L1 comprising the sequence of SEQ ID NO: 16, a CDR-L2 comprising the sequence of SEQ ID NO:18, and a CDR-L3 comprising the sequence of SEQ ID NO:19.

26. The antibody or antigen-binding portion of claim 1, wherein the heavy chain variable region comprises a CDR-H1 comprising the sequence of SEQ ID NO:12, a CDR-H2 comprising the sequence of SEQ ID NO:13, and a CDR-H3 comprising the sequence of SEQ ID NO:14; and wherein the light chain variable region comprises a CDR-L1 comprising the sequence of SEQ ID NO: 17, a CDR-L2 comprising the sequence of SEQ ID NO:18, and a CDR-L3 comprising the sequence of SEQ ID NO:19.

27. The antibody or antigen-binding portion of claim 1, wherein the binding affinity of such antibody or antigen-binding portion to sLeA is of $K_D$ of 60 μM or less and the binding affinity to sLeC is of $K_D$ 100 μM or less.

* * * * *